US012635850B2

(12) United States Patent
Sappati Biyyani

(10) Patent No.: US 12,635,850 B2
(45) Date of Patent: May 26, 2026

(54) SPHINCTEROTOME CANNULATION WITH NON-INVASIVE VISUALIZATION CAPABILITIES AND ENDOSCOPIC RETROGRADE CHOLANGIO PANCREATOGRAPHY WITH ARTIFICIAL INTELLIGENCE

(71) Applicant: Gastronaut LLC, Marietta, GA (US)

(72) Inventor: Raja Shekhar Reddy Sappati Biyyani, Marietta, GA (US)

( * ) Notice: Subject to any disclaimer, the term of this patent is extended or adjusted under 35 U.S.C. 154(b) by 504 days.

(21) Appl. No.: 18/120,349

(22) Filed: Mar. 10, 2023

(65) Prior Publication Data

US 2023/0284877 A1     Sep. 14, 2023

Related U.S. Application Data

(60) Provisional application No. 63/318,459, filed on Mar. 10, 2022.

(51) Int. Cl.
*A61B 1/00* (2006.01)
*A61B 1/018* (2006.01)

(52) U.S. Cl.
CPC ............ *A61B 1/0008* (2013.01); *A61B 1/018* (2013.01)

(58) Field of Classification Search
CPC ... A61B 1/0008; A61B 1/018; A61B 1/00098; A61B 1/000096; A61B 1/000094; A61B 1/273; A61B 1/2736; A61B 1/012
See application file for complete search history.

(56) References Cited

U.S. PATENT DOCUMENTS

| | | | | |
|---|---|---|---|---|
| 2002/0049423 A1* | 4/2002 | Howell | ................ | A61M 25/01 |
| | | | | 604/528 |
| 2005/0272975 A1* | 12/2005 | McWeeney | ............ | A61B 1/307 |
| | | | | 600/172 |
| 2006/0149129 A1* | 7/2006 | Watts | ................ | A61M 25/0152 |
| | | | | 600/113 |
| 2010/0081875 A1* | 4/2010 | Fowler | ................... | A61B 1/041 |
| | | | | 600/114 |
| 2019/0311478 A1* | 10/2019 | Avendi | ...................... | G06T 7/11 |
| 2019/0380565 A1* | 12/2019 | DeVries | ................ | A61B 1/015 |
| 2020/0193594 A1* | 6/2020 | Georgescu | ................ | G06T 7/11 |
| 2021/0169576 A1* | 6/2021 | Yoshinaka | ............ | G06N 20/00 |

* cited by examiner

*Primary Examiner* — Timothy J Neal
(74) *Attorney, Agent, or Firm* — Nova IP Solutions LLC

(57) ABSTRACT

The present disclosure relates to systems and methods for sphincterotome device with visualization capabilities. The distal tip section of the sphincterotome device has a diameter of about 5 fr and is controlled by a control wire to bend to a variety of degrees. The present disclosure further relates to systems and methods for artificial intelligence (AI) aided ERCP procedures and a combination of sphincterotome with visualization capabilities and AI aided ERCP procedures.

17 Claims, 13 Drawing Sheets

Working channel
of ERCP
Distal tip section

Control
wire

A

A

ERCP
Scope

Electronic display

Two LED lights

Image sensor

Two irrigation channels

Working channel for accessories and aspiration

Working channel

Channel opening

LCD camera

Working channel

Channel opening

Ultrasonic probe

Ultrasonic probe

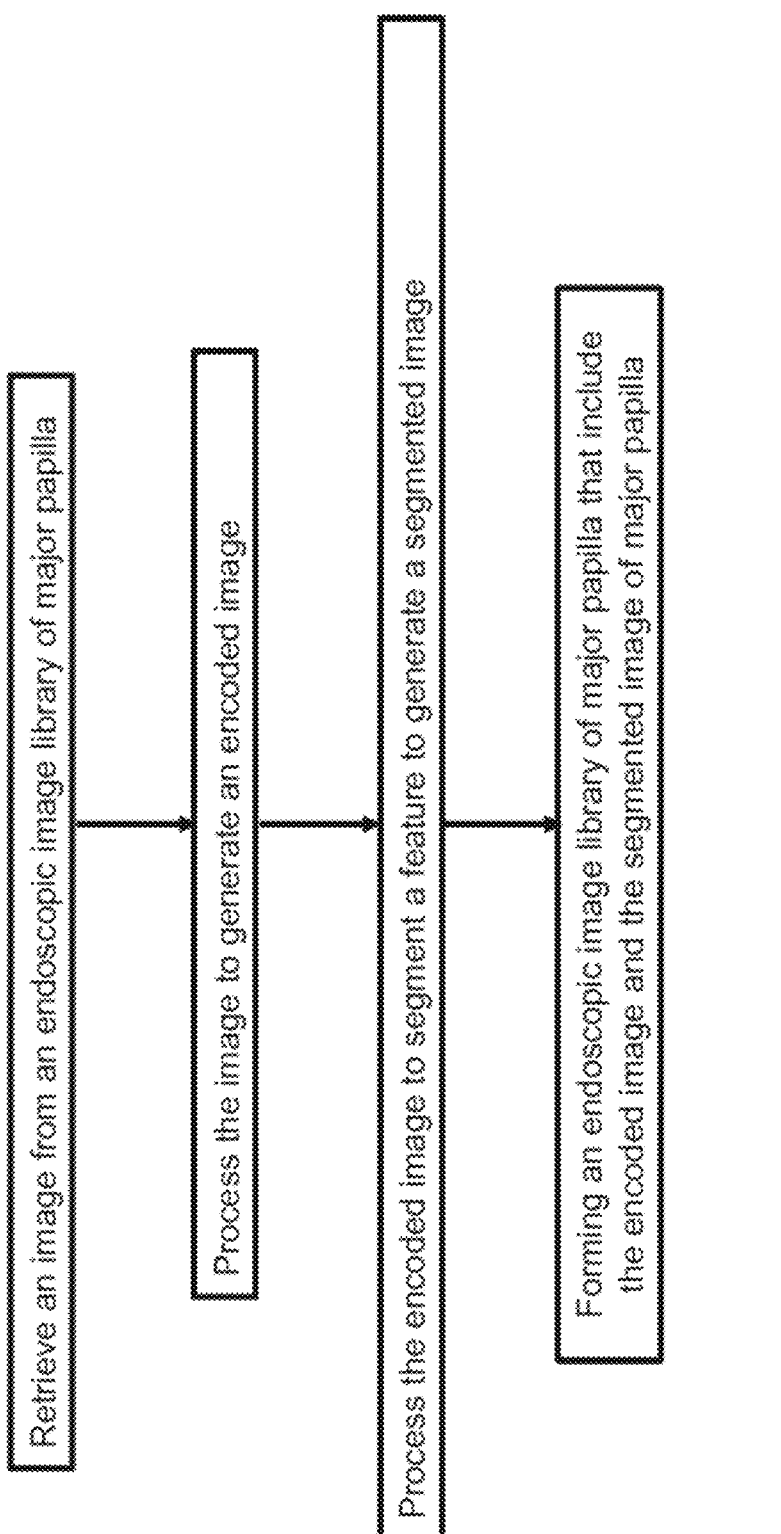
FIG. 8

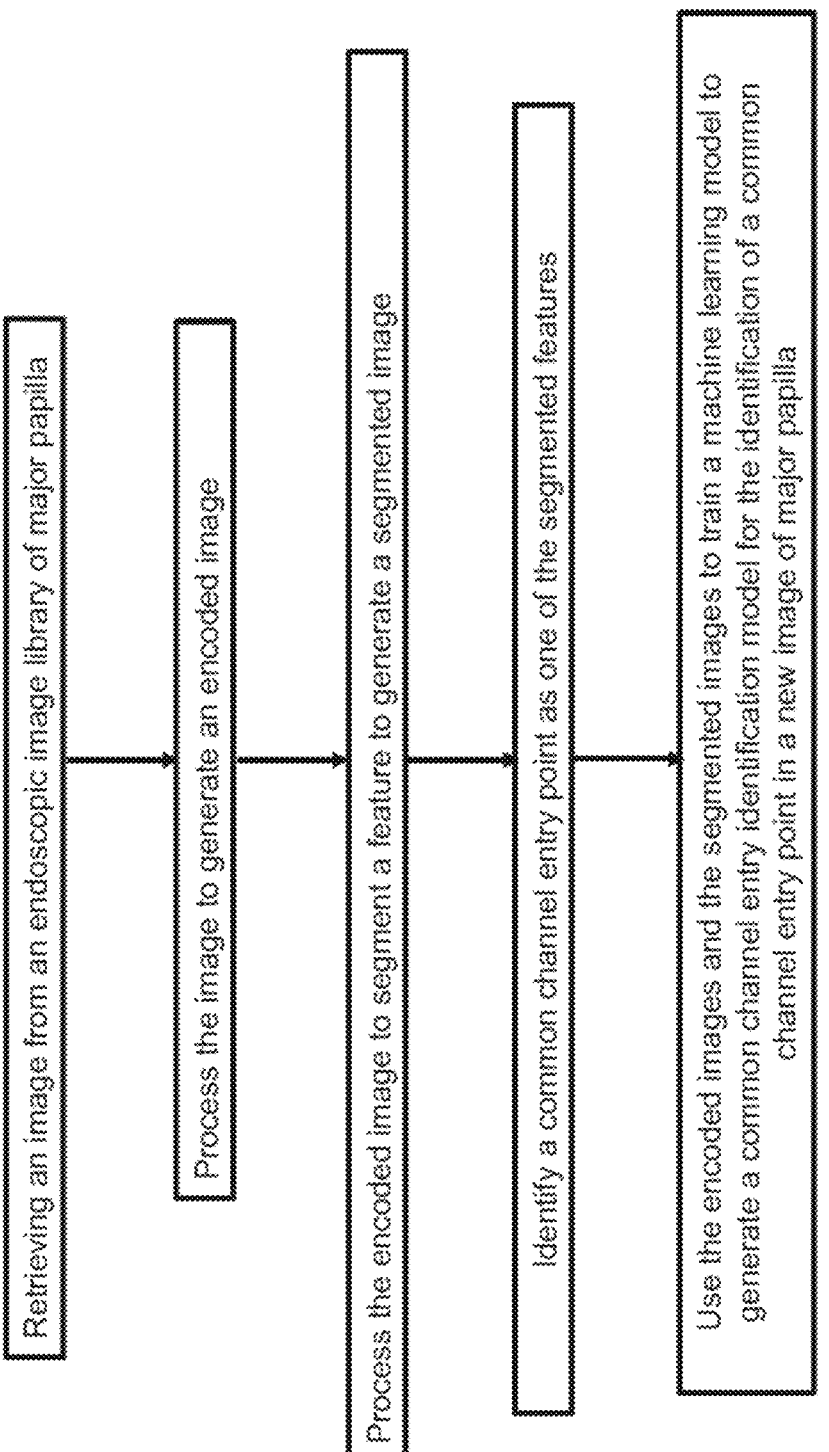

Retrieving an image from an endoscopic image library of major papilla

Process the image to generate an encoded image

Process the encoded image to segment a feature to generate a segmented image

Identify a common channel entry point as one of the segmented features

Use the encoded images and the segmented images to train a machine learning model to generate a common channel entry point identification model for the identification of a common channel entry point in a new image of major papilla

FIG. 9

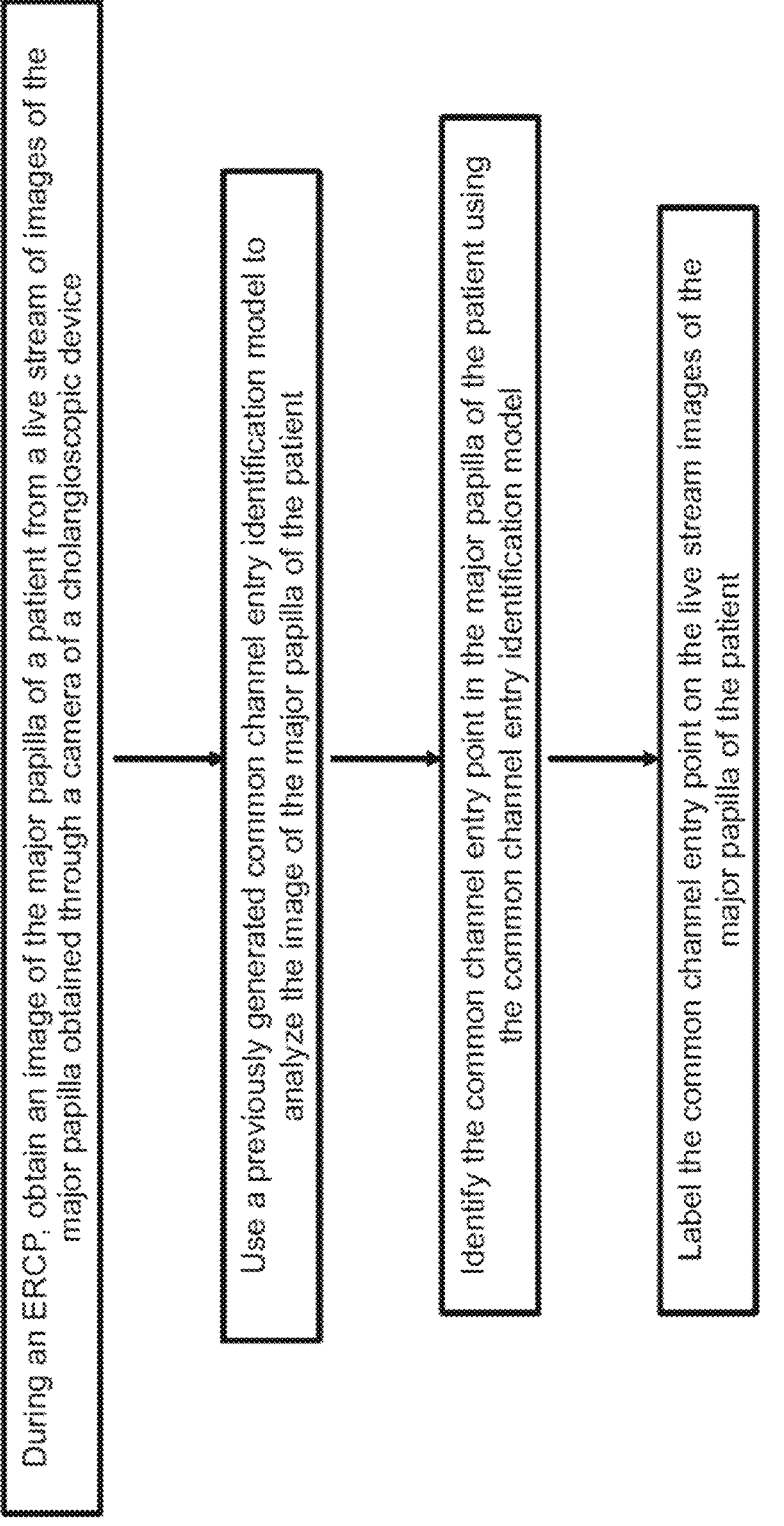

During an ERCP, obtain an image of the major papilla of a patient from a live stream of images of the major papilla obtained through a camera of a cholangioscopic device Use a previously generated common channel entry identification model to analyze the image of the major papilla of the patient Identify the common channel entry point in the major papilla of the patient using the common channel entry identification model Label the common channel entry point on the live stream images of the major papilla of the patient

FIG. 10

SPHINCTEROTOME CANNULATION WITH NON-INVASIVE VISUALIZATION CAPABILITIES AND ENDOSCOPIC RETROGRADE CHOLANGIO PANCREATOGRAPHY WITH ARTIFICIAL INTELLIGENCE

TECHNICAL FIELD

The present disclosure is directed to sphincterotome cannulation with non-invasive visualization capabilities, such as Endoscopic Retrograde Cholangio Pancreatography (ERCP) scope and methods of making and using such device. The present disclosure is also directed to a combination of sphincterotome cannulation with non-invasive visualization capabilities and with artificial intelligence, and a method of making and using a combination of sphincterotome cannulation with non-invasive visualization capabilities and with artificial intelligence.

BACKGROUND

Endoscopic Retrograde Cholangio Pancreatography (ERCP) is an endoscopic procedure performed by gastroenterologists to treat diseases of the bile duct and pancreas. Examples of bile duct diseases include bile duct stones, benign and malignant biliary strictures. ERCP is also performed to evaluate and treat pancreatic diseases including pancreatic duct strictures, pancreatic duct stones and pancreas divisum.

ERCP is a complicated and difficult endoscopic procedure done using a side-viewing scope. Cannulation of the desired duct often requires using a blind sphincterotome device to perform multiple blind directional probing to "fall" into the desired duct. Repeated blind probing can cause trauma to the sphincter pancreaticus resulting in post ERCP pancreatitis. There is a 5% risk of pancreatitis with any ERCP procedures and especially high risk (almost approaching 40%) in young women. Similarly, blind probing traumatizes the sphincter choledochus causing edema and subsequent inability to cannulate the bile duct. Therefore, prolonged cannulation attempts lead to above complications, prolonged procedure time and exposure to radiation and eventually leading to procedure failure. Prompt cannulation without ampullary trauma of the desired duct such as common channel, the bile duct, and the pancreatic duct is the key to ERCP success.

There exists a need for a sphincterotome device with enhanced visualization capabilities.

SUMMARY

In a first aspect, provided herein is a sphincterotome device with visualization capabilities (also referred to as the cholangioscopic device throughout the disclosure). The device comprises a user operation section, comprising one or more operation knobs and one or more ports; and an insertion section, comprising a tubular member for inserting into a tubular member of an Endoscopic Retrograde Cholangio Pancreatography (ERCP) scope. The insertion section of the device comprises a bendable tip section that comprises an image sensor, a working channel, and a control wire for control the direction of bendable tip section, with the image sensor, the working channel, and the control wire each operably connected to the user operation section of the device.

In one embodiment, the bendable tip section of the device further comprises an irrigation channel operably connected to the user operation section of the device and the working channel is configured for aspiration. In one embodiment, the image sensor is configured to capture images and transmit the captured images to a computing device for processing and display. In one embodiment, the device comprises or is interfaced with a controlling device at the user operation section of the device to operate the control wire to control the direction of the bendable distal section of the device. In one embodiment, the imaging sensor is a camera and the bendable tip section further comprises an illumination source that is operably connected to the user operation section of the device. In one embodiment, the image sensor is an ultrasonic probe.

In a second aspect, provided herein is a method of using the cholangioscopic device disclosed here. The method comprises the steps of inserting an Endoscopic Retrograde Cholangio Pancreatography (ERCP) scope into a duodenum of a patient until the ERCP scope identify major papilla of the patient; inserting the insertion section of the device of claim 1 into a working channel of the ERCP scope until the distal bendable tip section of the device exits the working channel and enters the duodenum, close to the major papilla; using an image sensor of the device to capture images of the major papilla; analyzing the images to identify an entry point of a common channel that leads to a common bile duct and a pancreatic duct; and adjusting the control wire to direct a tip of the bendable tip section towards the entry point; and inserting a guidewire into the working channel of the device to enter the entry point of the common duct. In one embodiment, the image analysis is done by a computational device in communication with the ERCP scope and the cholangioscopic device. In one embodiment, the bendable tip section of the cholangioscopic device further comprises an irrigation channel operably connected to the user operation section of the cholangioscopic device and the working channel is configured for aspiration and the method further comprises injecting rinsing liquid into the irrigation channel and aspiring the rinsing liquid from the working channel to rinse the major papilla. In one embodiment, the images of the major papilla are generated using the device that has camera as the image sensor. In one embodiment, the images of the major papilla are generated using the device that has ultrasonic probe as the image sensor.

In a third aspect, provided herein is a method of generating a common channel entry identification model using a computational device that comprises a processor, a non-transitory computer-readable storage medium storing a set of instructions, and a communication module connected to a network. The method comprises executing the set of instructions to direct the processor to: retrieve an image from an endoscopic image library of major papilla; process the image to generate an encoded image; process the encoded image to segment a feature to generate a segmented image; identify a common channel entry point as one of the segmented features; and use the encoded images and the segmented images to train a machine learning model to generate a common channel entry identification model for the identification of a common channel entry point in a new image of major papilla.

In one embodiment, the method further comprises obtaining a plurality of images of major papilla using a ERCP scope, the plurality of images including treatment-naïve images of major papilla and images of major papilla after cannulation of the common channel, to generate the endoscopic image library of the major papilla. In one embodiment, the images of the major papilla are taken under the same or similar conditions of the ERCP scope. In one embodiment, the same or similar conditions of the ERCP scope including number of time the major papilla has been rinsed with a rinsing fluid, the amount of illumination light supplied to the image sensor, parameters used by the image sensor. In one embodiment, the method further comprises obtaining a plurality of images of major papilla using an ultrasound device interfaced the ERCP scope, the plurality of ultrasound images including treatment-naïve images of major papilla and images of major papilla after cannulation of the common channel, to add to the endoscopic image library of the major papilla.

In a fourth aspect, provided herein is a method of labeling an estimated duct entry point in a new image of major papilla of a patient during an ERCP using a computational device that comprises a processor; a non-transitory computer-readable storage medium storing a set of instructions; and a communication module connected to a network. The method comprises executing the set of instructions to direct the processor to: obtain an image of the major papilla of a patient from a live stream of images of the major papilla obtained through a camera of ERCP scope; use a common channel entry identification model generated to analyze the image of the major papilla of the patient; identify the common channel entry point in the image of the major papilla of the patient using the common channel entry identification model; and label the common channel entry point on the live stream images of the major papilla of the patient. In one embodiment, the image of the major papilla of the patient is taken under the same or similar conditions of the images used to train the common channel entry identification model. In one embodiment, the method further comprises inserting a guidewire from a working channel of the ERCP device to the estimated duct entry point to enter the common duct.

In a fifth aspect, provided herein is a cholangioscopic device with artificial intelligence capabilities that comprises a user operation section, comprising one or more operation knobs and one or more ports; an insertion section, comprising a tubular member for inserting into a tubular member of an Endoscopic Retrograde Cholangio Pancreatography (ERCP) scope; and a computational component that comprises a processor, a non-transitory computer-readable storage medium storing a common channel entry identification model and a set of instructions, and a communication module connected to a network. The insertion section of the cholangioscopic device with artificial intelligence capabilities has a bendable tip section that comprises: an image sensor; a working channel; and a control wire for control the direction of bendable tip section, each operably connected to the user operation section of the cholangioscopic device with artificial intelligence capabilities. The image sensor of the cholangioscopic device with artificial intelligence capabilities is configured to capture images and transmit the captured images to the computational component for processing and display.

In a fifth aspect, provided herein is a method of using a cholangioscopic device with artificial intelligence capabilities. The method comprises the steps of inserting an Endoscopic Retrograde Cholangio Pancreatography (ERCP) scope into the duodenum of a patient until the ERCP scope identify major papilla of the patient; inserting the insertion section of the device into a working channel of the ERCP scope until the distal bendable tip section of the device exits the working channel and enters the duodenum, close to the major papilla; using the image sensor of the device to capture images of the major papilla; analyzing the images to identify an entry point of a common channel that leads to a common bile duct and a pancreatic duct; using the common channel entry identification model stored in the computational component to analyze the image of the major papilla of the patient; identifying the common channel entry point in the image of the major papilla of the patient using the common channel entry identification model; label the common channel entry point on the live stream images of the major papilla of the patient; adjusting the control wire to direct a tip of the bendable tip section towards the labeled entry point; and inserting a guidewire into the working channel of the device to enter the common duct.

BRIEF DESCRIPTION OF THE DRAWINGS

The drawing figures are not necessarily to scale and certain features may be shown exaggerated in scale or in a somewhat generalized or schematic form in the interest of clarity and conciseness. For more complete understanding of the features and advantages of the present invention, reference is now made to the detailed description along with the accompanying figures, wherein:

FIG. 8 is a flow chart showing the process to use the images from the endoscopic image library of major papilla of FIG. 7 to train a machine learning model to generate a feature identification model for the identification of the feature in a new image of major papilla.

FIG. 9 is a flow chart showing the process to use the images from the endoscopic image library of major papilla of FIG. 7 to train a machine learning model to generate a common channel entry identification model for the identification of a common channel entry point in a new image of major papilla.

FIG. 10 is a flow chart showing the process to Identify the common channel entry point in the major papilla of a patient using the common channel entry identification model of FIG. 9.

DETAILED DESCRIPTION

Definitions

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a composition that "comprises," "has," "includes" or "contains" one or more elements possesses those one or more elements but is not limited to possessing only those elements. Likewise, a method that "comprises," "has," "includes" or "contains" one or more steps possesses those one or more steps but is not limited to possessing only those one or more steps.

The sphincterotome device with visualization capabilities disclosed herein is also referred to as the cholangioscopic device throughout the specification.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Throughout this application, various publications are referenced. The disclosures of these publications in their entire-ties are hereby incorporated by reference into this application in order to more fully describe the state of the art to which this pertains. The references disclosed are also individually and specifically incorporated by reference herein for the material contained in them that is discussed in the sentence in which the reference is relied upon.

The present disclosure may be understood more readily by reference to the following detailed description of embodiments and to the Figures and their previous and following description.

Figures 1A, 1B:
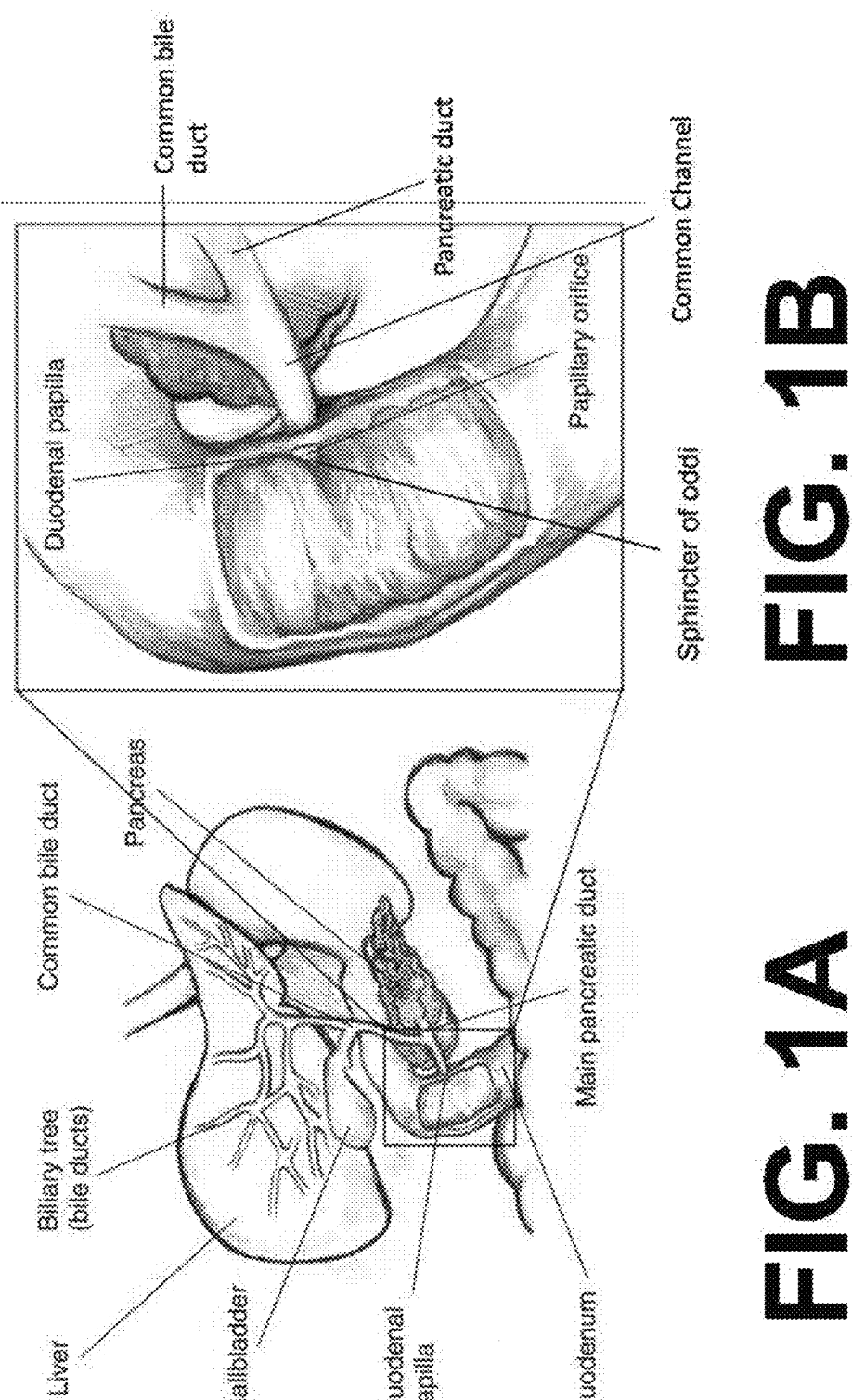
FIG. 1A is a schematic diagram of the anatomy of liver, gallbladder, and pancreas in relationship to duodenum.
FIG. 1B is a schematic diagram of an enlarged portion of FIG. 1A showing the anatomy of the bile and pancreatic ducts connected to a common channel of major papilla that is visible in duodenum.

Referring to FIG. 1A, a schematic diagram of the anatomy of liver, gallbladder, and pancreas in relationship to duodenum is shown. The duodenum is a portion of a small intestine where the secretion or juice of the bile and pancreatic ducts enters the digestive tract. FIG. 1B is an enlarged view of a portion of FIG. 1A. As shown in FIG. 1B, the orifice of major duodenal papilla (papilla of Vater) of the small intestine is the point where the dilated junction of the bile and pancreatic ducts (ampulla of Vater) enter the second portion of duodenum. The orifice is surrounded by sphincter of oddi, which not only controls the flow of bile and pancreatic juice into the duodenum, but also prevents the reflux of duodenal contents, bile and pancreatic juice into the bile and pancreatic ducts.

Figure 2:
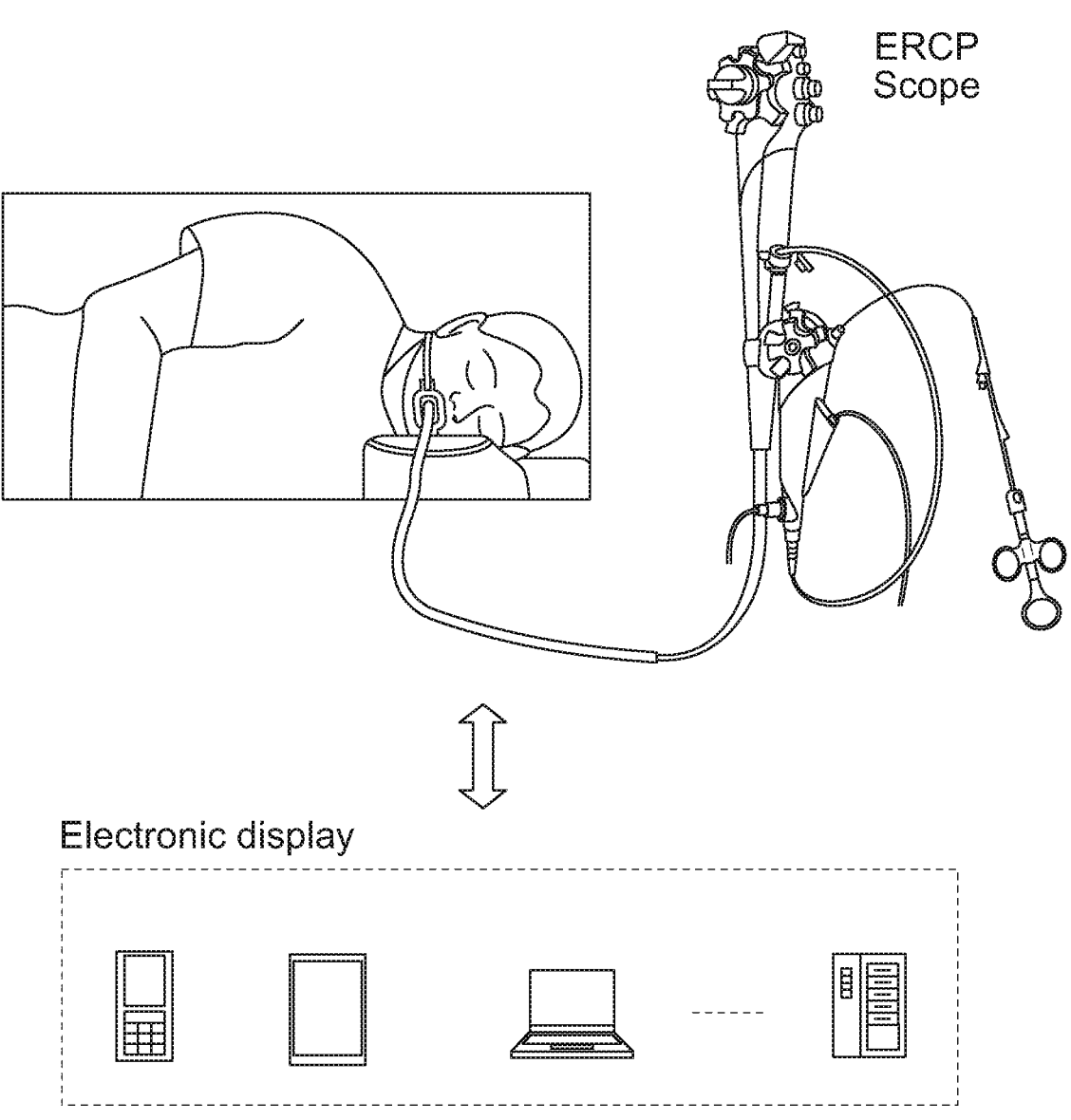
FIG. 2 is a schematic diagram, showing a patient being treated with ERCP that has an electronic display.
Figures 2A, 2B, 2C:
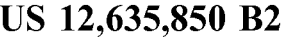
FIG. 2A is a schematic diagram of a sphincterotome device or guidewire entering the major papilla of FIG. 1B.
FIG. 2B is a schematic diagram of a sphincterotome device or guidewire entering the common bile duct of FIG. 1B.
FIG. 2C is a schematic diagram of a sphincterotome device or guidewire entering the pancreatic duct of FIG. 1B.

During an ERCP, as shown in FIG. 2, the major duodenal papilla of a patient is viewed through an ERCP scope. Images captured by the ERCP scope is transmitted to an electronic display for viewing, for example by an operator operating the ERCP scope. The visualized major papilla is then accessed by a sphincterotome device via a working channel of the ERCP. As show in FIG. 2A, the orifice of major duodenal papilla is accessed with a sphincterotome device or guidewire to enter the common channel first. Then, the common bile duct is accessed by a sphincterotome device or guidewire via the sphincter choledochus as shown in FIG. 2B or the pancreatic duct is accessed by a sphincterotome device or guidewire via the sphincter pancreaticus as shown in FIG. 2C. Fluoroscopy generally is used to visualize the trajectory of the guidewire during an ERCP procedure. For diagnostic and therapeutic procedures, cannulation of either the bile duct or the pancreatic duct has been performed based on fluoroscopy visual estimation and feel and therefore often requires multiple blind directional probing to "fall" into the desired duct. Repeated blind probing can cause trauma during an ERCP procedure. For example, during the cannulation attempts of the pancreatic duct, trauma may occur to the sphincter pancreaticus and resulting in post ERCP pancreatitis. It has been estimated that there is a 5% risk of pancreatitis with any ERCP procedures and especially high risk (almost approaching 40%) in young women. Similarly, blind probing traumatizes the sphincter choledochus causing edema and subsequent inability to cannulate the bile duct. Prolonged cannulation attempts lead to not only the above complications, but they also tend to lead to prolonged procedure time and exposure to radiation and eventually leading to procedure failure. Prompt cannulation with minimal ampullary trauma of the desired duct such as common bile duct and pancreatic duct for therapy is therefore the key to ERCP success.

Anatomic variations also exist in the apertures of pancreatic and biliary ducts, which further complicates the cannulation of either one of the pancreatic and biliary ducts. The apertures of pancreatic and bile ducts can be classified as follows: multiple duodenal papillae in which the pancreatic and bile ducts are clearly separated, those that are joined to form a partition, and those that form a common duct. In fact, studies have revealed that only 55-86% of individuals have a common duct.

Disclosed herein is a Direct Visual Cannulation (DVC) approach to use a direct visualization device such as a camera or a doppler ultrasound to directly visualize a cannulation entry point such as an opening or orifice to facilitate an ERCP procedure. Once the cannulation entry point is visualized by the direct visualization device, the probability of a successful cannulation at the cannulation entry point is significant increased. Visualizing the opening allows for more prompt cannulation of the desired bile duct and pancreatic duct. This will reduce the procedure time thereby decreasing radiation exposure, reduce tissue trauma thereby decreasing risk of ERCP related complications, procedure failure rate and possibly also the infection risk.

Figures 3, 4A, 4B:
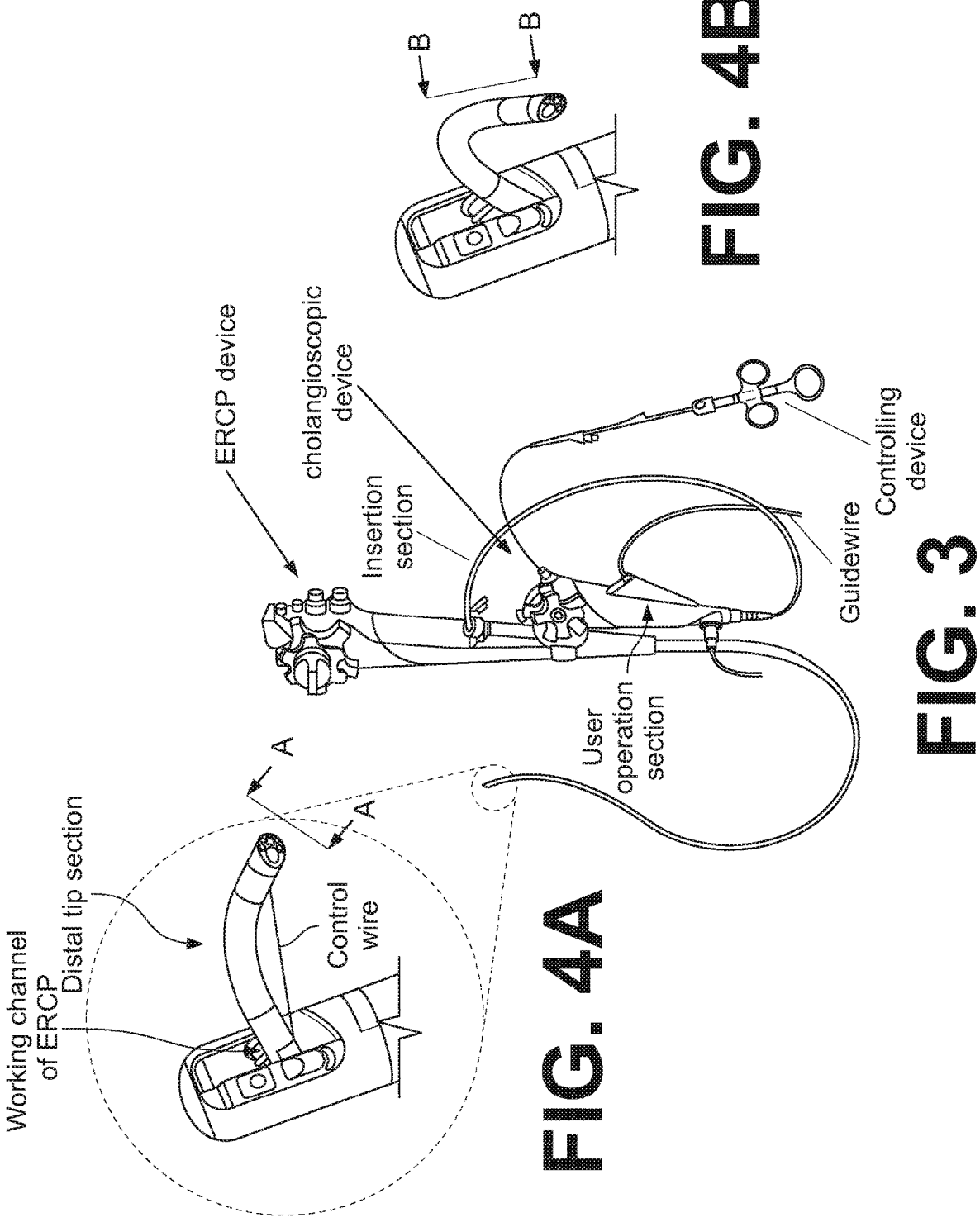
FIG. 3 is a schematic diagram of an ERCP scope interfaced with a cholangioscopic device according to one embodiment of the present disclosure.
FIG. 4A is a schematic diagram of an enlarged view of the tip of the ERCP scope interfaced with the cholangioscopic device of FIG. 3, showing the tip of the cholangioscopic device exiting the tip of the ERCP scope, the tip of the cholangioscopic device having a control wire.
FIG. 4B is a schematic diagram of the enlarged view of the tip of the ERCP scope, showing the tip of the cholangioscopic device in FIG. 4A being bend by a shortened control wire.

In one embodiment, disclosed herein is a cholangioscopic device having an ability to image the major papilla and the entry point of a desired duct. Referring to FIG. 3, a cholangioscopic device according to one embodiment of the present disclosure is shown interfaced with a ERCP scope. The cholangioscopic device comprises a user operation section and an insertion section. The user operation section comprises knobs for operating various components of the cholangioscopic device and ports for interfacing with other devices or functions. In some embodiments, as shown in FIG. 3, the cholangioscopic device has a port interfacing with a guidewire and another port interfacing with a controlling device. The insertion section of the cholangioscopic device is inserted into a working channel of an ERCP. FIG. 4A is an enlarged view of the distal tip of the ERCP, showing the distal tip section of the cholangioscopic device exiting the working channel of the ERCP, the distal tip section of the cholangioscopic device having a control wire. FIG. 4B is an enlarged view of the distal tip of the ERCP, showing the tip of the cholangioscopic device in FIG. 4A being bend by a shortened control wire. In one embodiment, the control wire is controlled by the controlling device shown in FIG. 3. Details of the distal tip section of the cholangioscopic device can be seen in FIGS. 5A and 5B which are views of the device along the A-A line of FIG. 4A and the B-B line of FIG. 4B, respectively.

Figure 5A:
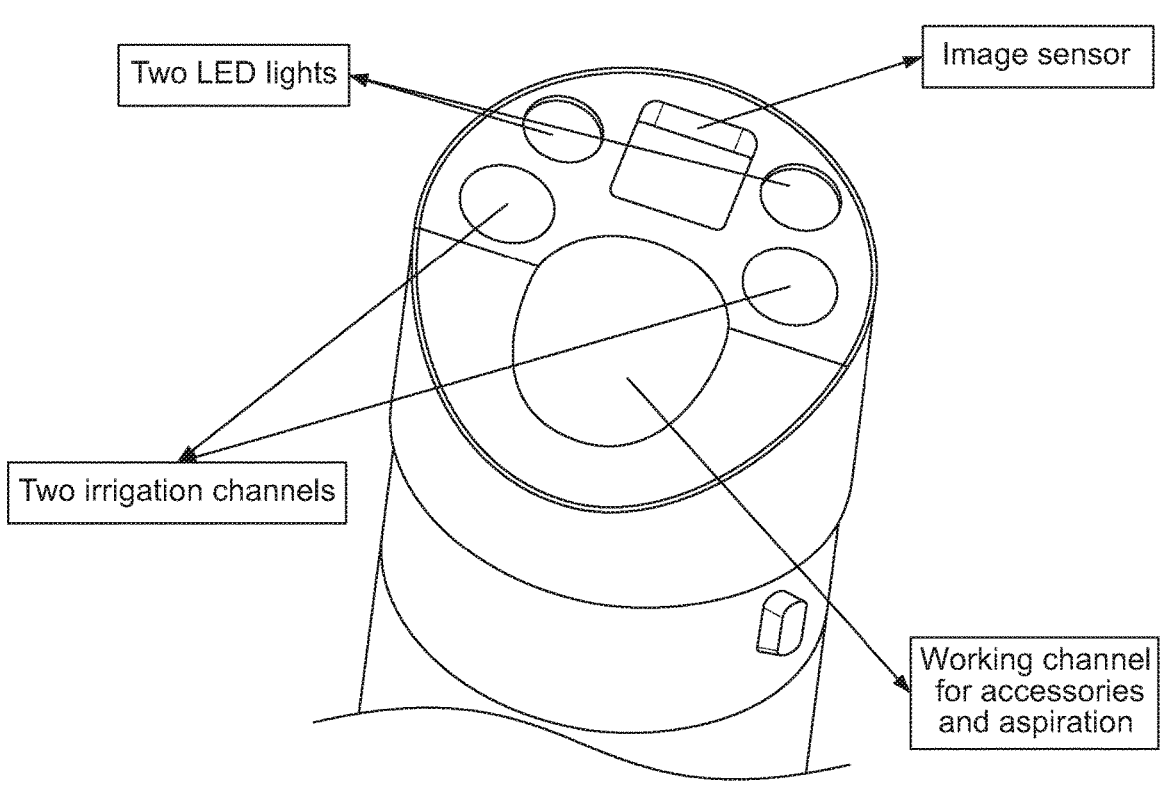
FIG. 5A is a schematic diagram, showing a front view of the distal tip of the cholangioscopic device along the A-A line of FIG. 4A.
Figure 13:
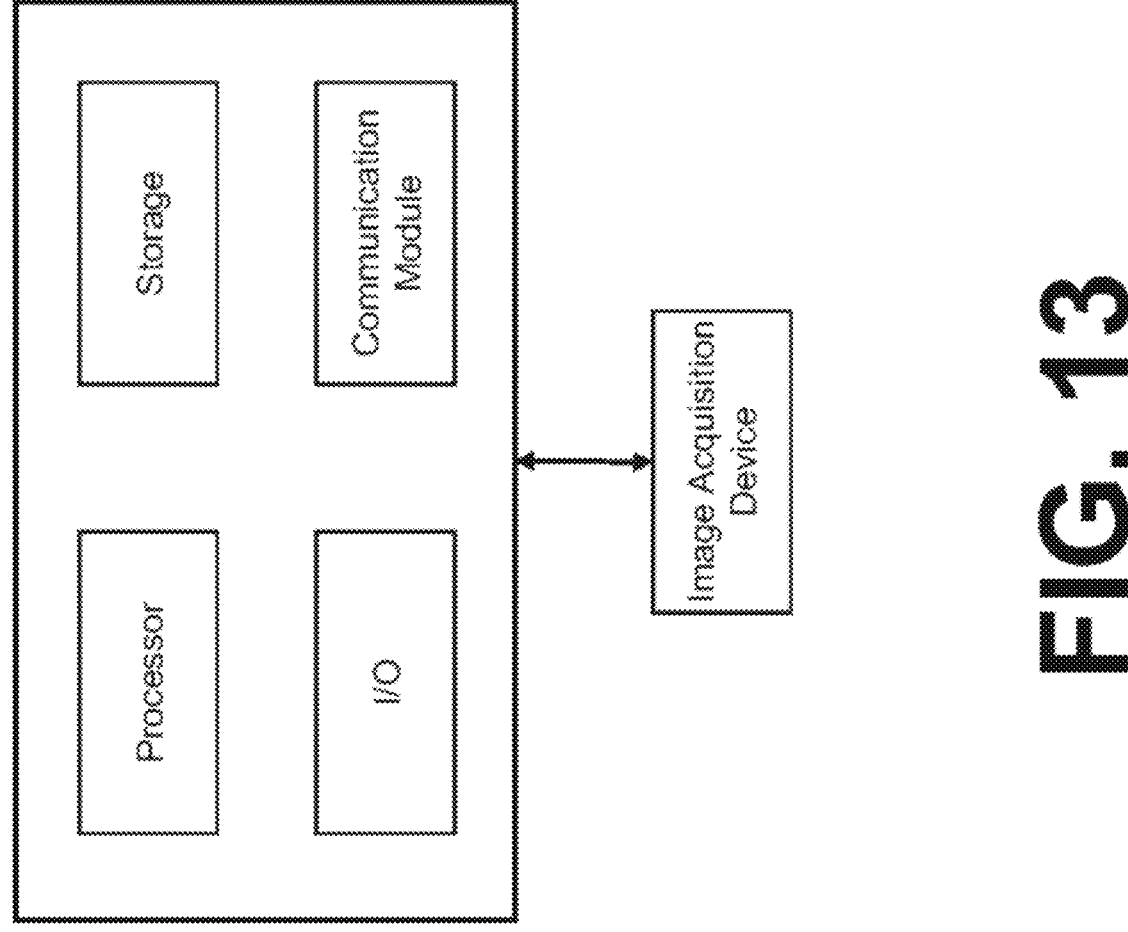
FIG. 13 is a schematic diagram, showing a computational device in communication with an image acquisition device.

FIG. 5A is the front view of the tip of the insertion section of the cholangioscopic device, showing two LED lights, a digital image sensor, two irrigation channels, and a work channel for accessories and aspiration, according to one embodiment of the present disclosure. The image sensor, the illumination light, the working channel, and the control wire are each operably connected to the user operation section of the device. For example, the control wire is operably connected to the controlling device shown in FIG. 3. The illumination light is operably connected to a light source through the user operation section, for example, through an electrical cable. The same cable can be configured to transmit images captured by the image sensor. In one embodiment, the electrical cable extends from the user operation section to be connected to other electronic devices, such as a light source, or a computational device for image data processing and display. FIG. 13 shows an example computational device that is linked to image acquisition device such as an ERCP scope or a cholangioscopic device disclosed herein. In one embodiment, the user operation section further comprises a switch for performing operation of the computational device and a connected recording device.

Figure 5B:
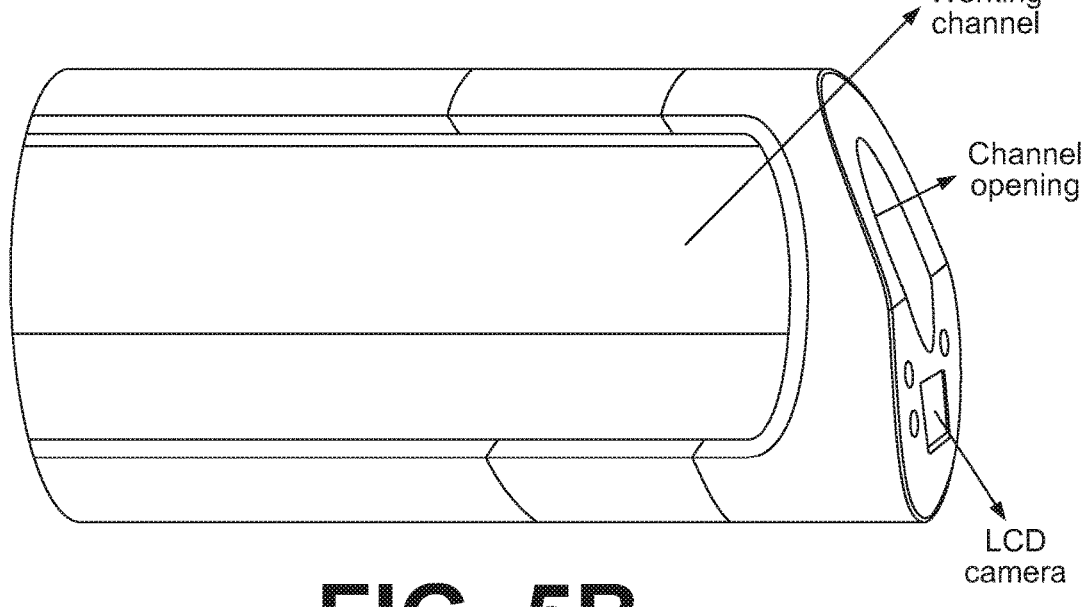
FIG. 5B is a schematic diagram, showing a cross-sectional view of the tip of the cholangioscopic device along the B-B line of FIG. 4B, with a camera as the image sensor, according to one embodiment of the present disclosure.

FIG. 5B is the side cross sectional view of the tip section of the insertion section of the cholangioscopic device, showing an LCD camera as the digital image sensor and a side view of the working channel and its opening, according to one embodiment of the present disclosure. Because the tip section of the insertion section of the cholangioscopic device can be controlled by the control wire, the LCD camera can be aimed at different areas of major papilla to obtain images of major papilla from different angles.

In some embodiments, the working channel of cholangioscopic device disclosed herein can be used for aspiration. In one embodiment, the major papilla of a patient can be rinsed by supply rinsing fluid through the irrigation channels of the cholangioscopic device to the major papilla. Once the rinsing period is complete, the rinsing fluid in the major papilla can be aspirated through the working channel of the cholangioscopic device.

Figure 5C:
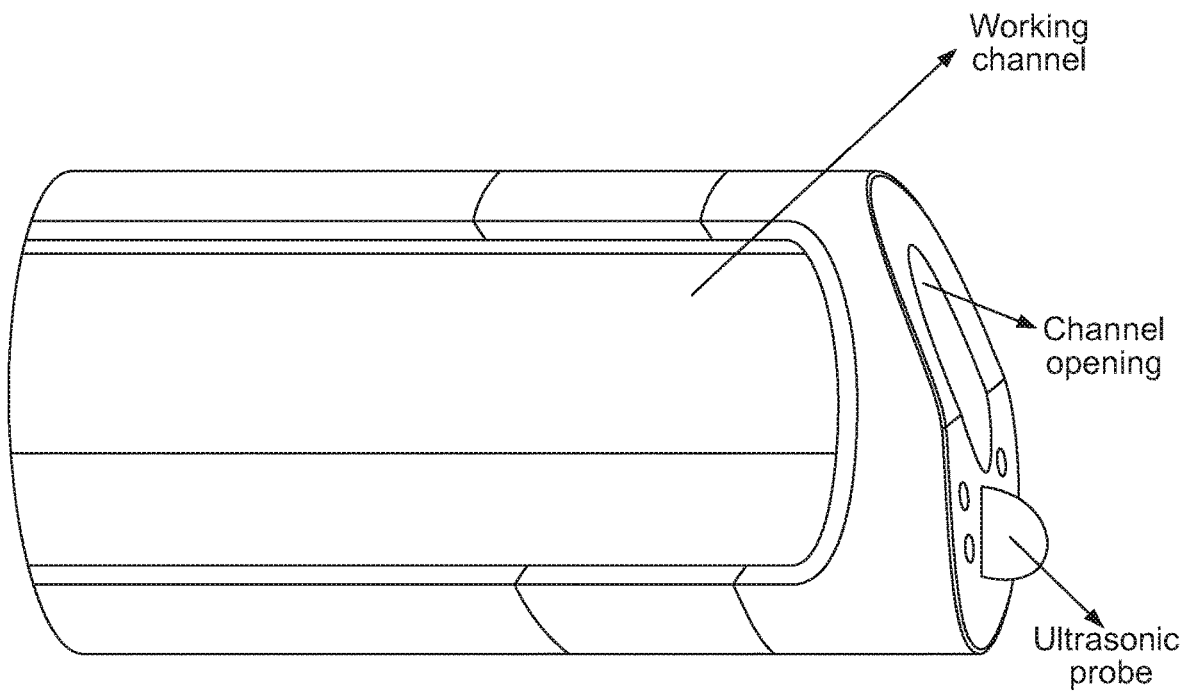
FIG. 5C is a schematic diagram, showing a cross-sectional view of the tip of the cholangioscopic device along the B-B line of FIG. 4B, with an ultrasonic probe as the image sensor, according to one embodiment of the present disclosure.
Figure 6:
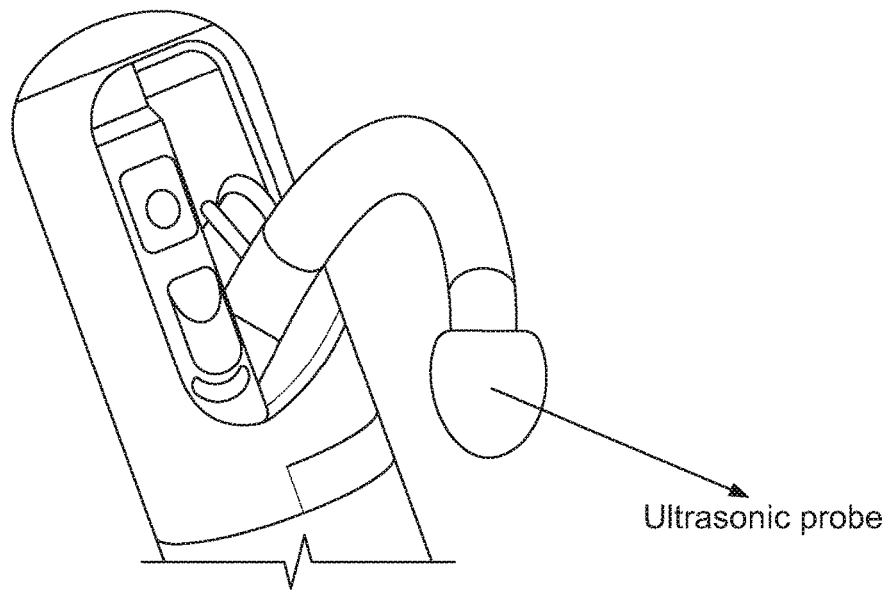
FIG. 6 is a schematic diagram, showing an ultrasound doppler probe exiting the working channel of the tip of the ERCP of FIG. 3.

The image sensor of the cholangioscopic device can also be an ultrasonic probe. For example, FIG. 5C is a schematic diagram, showing a cross-sectional view of the tip of the cholangioscopic device along the B-B line of FIG. 4B, with an ultrasonic probe as the image sensor, according to one embodiment of the present disclosure. In some embodiments, the distal tip of the cholangioscopic device comprises an ultrasonic probe that occupies the entire distal tip of the ultrasonic probe, as shown in FIG. 6. Because the tip section of the insertion section of the cholangioscopic device can be controlled by the control wire, the ultrasonic probe can be aimed at different areas of major papilla to obtain ultrasonic images of major papilla from different angels.

During an ERCP procedure, an Endoscopic Retrograde Cholangio Pancreatography (ERCP) scope is first inserted into a duodenum of a patient until the ERCP scope identify major papilla of the patient so that the tip of the ERCP scope can be placed close to the major papilla. The insertion section of the cholangioscopic device disclosed herein is then inserted into a working channel of the ERCP scope until the distal bendable tip section of the cholangioscopic device exits the working channel and enters the duodenum, close to the major papilla so an image sensor of the cholangioscopic device can capture images of the major papilla. The captured images by the cholangioscopic device are analyzed to identify an entry point of a common channel that leads to a common bile duct and a pancreatic duct. Once the entry point is identified, a control wire of the distal tip section of the cholangioscopic device can then be adjusted by the control device to aim a tip of the bendable tip section towards the entry point. In some embodiment, the captured images are not still images, but rather a live stream images of the major papilla that is continuously captured by the cholangioscopic device and displayed on an electronic display for visualization. In some embodiments, a live stream images of the major papilla that is continuously captured by the ERCP scope is also displayed on an electronic display for visualization. In some embodiments, the live stream of images of the major papilla from the ERCP and the cholangioscopic device are both displayed on the same electronic display for visualization of the major papilla. A guidewire can then be inserted into the working channel of the cholangioscopic device to enter the entry point of major papilla. Subsequently, the control wire of the bended tip of the tip section of the cholangioscopic device can then be relaxed and the cholangioscopic device can then enter the entry point of the major papilla, following the previously inserted guide wire. In one embodiment, the images of the cholangioscopic device are camera images. In another embodiment, the images of the cholangioscopic device are ultrasonic images.

Once delivered inside the common channel, the image sensor of the cholangioscopic device can capture images of the common channel or inside of the major papilla. The captured images by the cholangioscopic device are analyzed to identify an entry point of the common bile duct or the pancreatic duct. Once the entry point is identified, a control wire of the distal tip section of the cholangioscopic device can then be adjusted by the control device to aim a tip of the bendable tip section towards the entry point the common bile duct or the pancreatic duct. In some embodiment, the captured images are not still images, but rather a live stream images of the major papilla that is continuously captured by the cholangioscopic device and displayed on an electronic display for visualization. A guidewire can then be inserted into the working channel of the cholangioscopic device to enter the entry point of the common bile duct or the pancreatic duct. Subsequently, the control wire of the bended tip of the tip section of the cholangioscopic device can then be relaxed and the cholangioscopic device can then enter the entry point of the common bile duct or the pancreatic duct, following the previously inserted guide wire. In one embodiment, the images of the cholangioscopic device are camera images. In another embodiment, the images of the cholangioscopic device are ultrasonic images.

In some embodiment, the diameter of the tip section of the cholangioscopic device is around 5 Fr, for example, 4-4.25 fr, 4.25-4.5 fr, 4.5-4.75 fr, 4.75-5 fr, 5-5.25 fr, or 5.25 fr-5.5 fr.

In one embodiment, the ampulla surrounding the major papilla is interrogated with air versus normal water insufflation before the images are captured by the cholangioscopic device. In one embodiment, the interior of the major papilla is interrogated before the images are captured by the cholangioscopic device. The air can be supplied through the irrigation channel of cholangioscopic device.

The identification of the entry point of the major papilla can be further aided by using artificial intelligence (AI) based machine learning for predictive analysis in locating the entry point of the major papilla for more prompt cannulation to reduce the procedure time, thereby decreasing radiation exposure, reduce tissue trauma thereby decreasing risk of ERCP.

Figure 7:
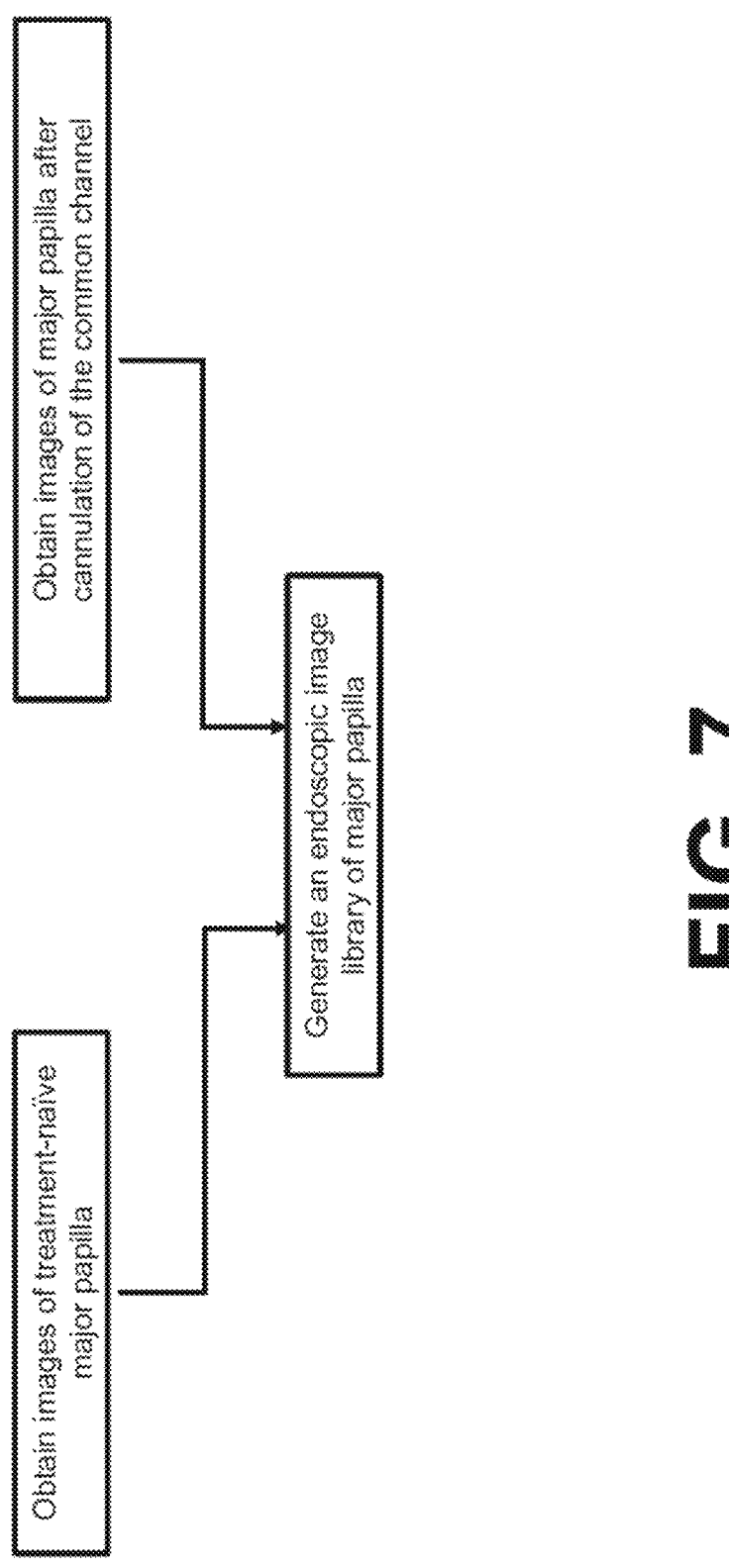
FIG. 7 is a flow chart showing the process to generate an endoscopic image library of major papilla.

Specifically, endoscopic images of the treatment naïve (no prior therapy performed on the major papilla) major papilla from an ERCP scope are collected during an ERCP procedure. Similarly, endoscopic images are taken after cannulation of the major papilla. Parametric data points in images of the ampulla and adjacent duodenum are processed by a computer to design an endoscopic image library of major papilla. The process of constructing an endoscopic image library of major papilla is illustrated in FIG. 7. In one embodiment, the endoscopic image library of major papilla comprises at least 50 endoscopic images of major papilla. In one embodiment, the endoscopic images of major papilla are collected at multiple endoscopic facilities and done by the multiple accomplished gastroenterology physicians.

Figure 12:
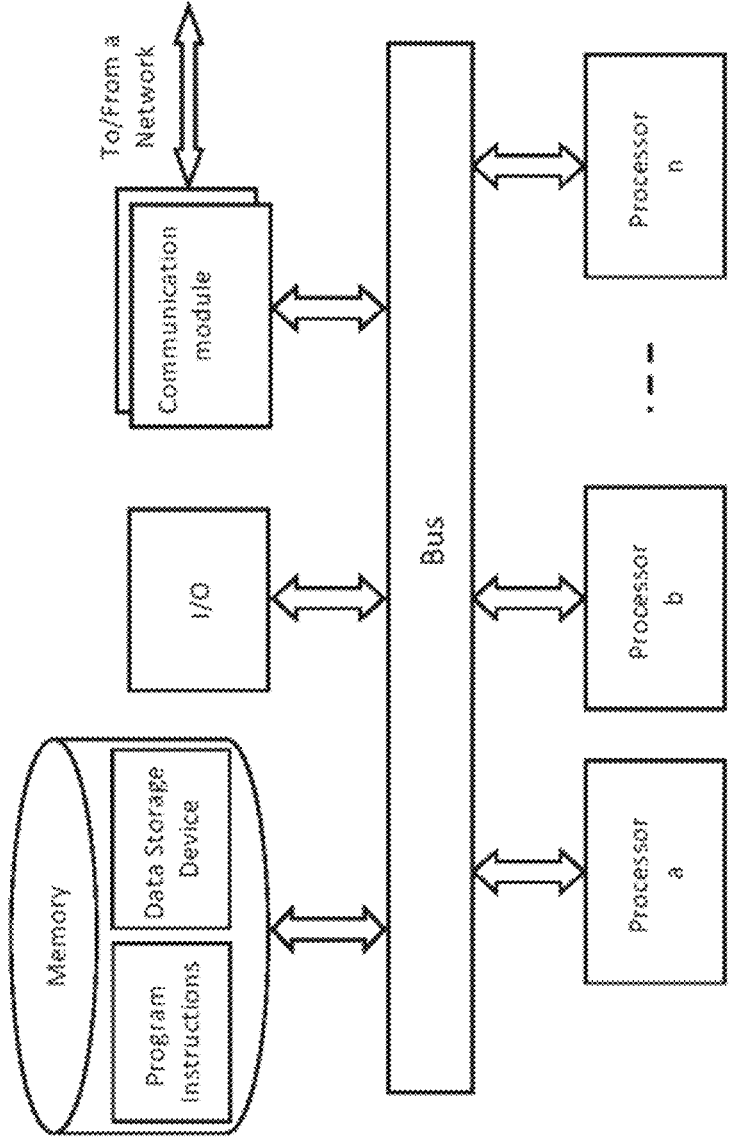
FIG. 12 is a schematic diagram, showing a computational device for generating a feature identification model based on machine learning algorithms.

Image from the endoscopic image library of major papilla can then be retrieved by a computation device such as the one shown in FIG. 12 for further processing. For example, the image processing comprise process the image to generate an encoded image. The encoded image can then be processed to segment a feature to generate a segmented image. In one embodiment, the feature is the entry point of major papilla. The encoded and segmented images can then be collected to form an endoscopic image library of major papilla including encoded and segmented images. The process of constructing an endoscopic image library of major papilla that includes encoded and segmented images is illustrated in FIG. 8.

In one embodiment, encoding of an image is performed by using an encoding neural network. In one embodiment, the encoding neural network is a convolutional neural network, for example on the computational device of FIG. 12. In one embodiment, to segment a feature to generate a segmented image is performed by segmenting an encoded image according to a first feature. The segmentation process is performed by using a segmentation neural network, such as a convolutional neural network.

The encoded images and the segmented images can then be used to train a machine learning model to generate a major papilla entry point identification model for the identification of a major papilla entry point in a new image of major papilla. The process of generating a major papilla entry point identification model is illustrated in FIG. 9.

Figure 11B:
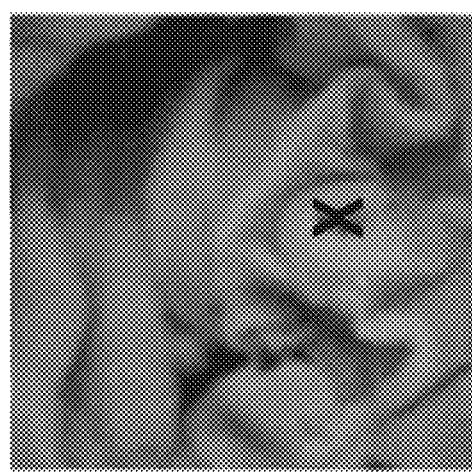
FIG. 11B is a stream of images of a major papilla marked by a label "X" according to the process of FIG. 10.
Figure 11A:
FIG. 11A is an image of major papilla taken by an ERCP scope.

After fully establishing the major papilla entry point identification model, when starting a new ERCP, the major papilla is identified and compared to the library of major papilla images. The probable area showing the entry point of the major papilla is then be displayed on the endoscopy screen to guide the endoscopist. The process of using a major papilla entry point identification model to analyze and label a new image of major papilla of a patient is illustrated in FIG. 10. And FIGS. 11A and 11B shows respectively the new image of major papilla of a patient before and after the superimposing of the label "X".

ERCP procedures using the AI model analysis and image labeling disclosed here decrease the time required for cannulation thereby decrease tissue trauma, post-ERCP complication rate and exposure time for fluoroscopy. Free hand needle-knife sphincterotomies can also be assisted with this software. In one embodiment, the new images of major papilla of the patient before and after the cannulation are added to the endoscopic image library of major papilla.

The present disclosure is directed to sphincterotome with visualization capabilities, and methods of using such device. The present disclosure is also directed to ERCP with artificial intelligence, and methods of performing ERCP with artificial intelligence. The present disclosure is further directed to a combination of sphincterotome with visualization capabilities and ERCP with artificial intelligence, and a method of using a combination of sphincterotome with visualization capabilities and ERCP with artificial intelligence.

The embodiments above are intended to be illustrative and not limiting. Additional embodiments are within the claims. In addition, although the present disclosure has been described with reference to particular embodiments, those skilled in the art will recognize that changes can be made in form and detail without departing from the spirit and scope of the disclosure. Any incorporation by reference of documents above is limited such that no subject matter is incorporated that is contrary to the explicit disclosure herein.

I claim:

1. A cholangioscopic device with artificial intelligence capabilities, comprising:
   a user operation section, comprising one or more operation knobs and one or more ports;
   an insertion section, comprising a tubular member for inserting into a tubular member of an Endoscopic Retrograde Cholangio Pancreatography (ERCP) scope; and
   a computational component that comprises a processor, a non-transitory computer-readable storage medium storing a common channel entry identification model and a set of instructions, and a communication module connected to a network,

wherein the insertion section comprising a bendable tip section that comprises:

an image sensor;

a working channel; and a control wire for control the direction of bendable tip section, wherein the image sensor, the working channel, and the control wire are each operably connected to the user operation section of the device, wherein the image sensor is configured to capture images and transmit the captured images to the computational component for processing and display, and wherein the common channel entry identification model is trained by images of both treatment naïve major papilla and major papilla after cannulation of the common channel.

2. The device of claim 1, wherein the bendable tip section further comprising an irrigation channel operably connected to the user operation section of the device and the working channel is configured for aspiration.

3. The device of claim 1, wherein the image sensor is configured to capture images and transmit the captured images to a computing device for processing and display.

4. The device of claim 1, further comprising or interfacing with a controlling device at the user operation section of the device to operate the control wire to control the direction of the bendable distal section of the device.

5. The device of claim 1, wherein the imaging sensor is a camera and the bendable tip section further comprises an illumination source that is operably connected to the user operation section of the device.

6. The device of claim 1, wherein the image sensor is an ultrasonic probe.

7. A method of using the device of claim 1, the method comprising:

inserting an Endoscopic Retrograde Cholangio Pancreatography (ERCP) scope into the duodenum of a patient until the ERCP scope identify major papilla of the patient;

inserting the insertion section of the device into a working channel of the ERCP scope until the distal bendable tip section of the device exits the working channel and enters the duodenum, close to the major papilla;

using the image sensor of the device to capture images of the major papilla; analyzing the images to identify an entry point of a common channel that leads to a common bile duct and a pancreatic duct;

using the common channel entry identification model stored in the computational component to analyze the image of the major papilla of the patient;

identifying the common channel entry point in the image of the major papilla of the patient using the common channel entry identification model;

labeling the common channel entry point on the live stream images of the major papilla of the patient;

adjusting the control wire to direct a tip of the bendable tip section towards the labeled entry point; and inserting a guidewire into the working channel of the device to enter the common duct.

8. The method of claim 7, wherein the bendable tip section of the device further comprising an irrigation channel operably connected to the user operation section of the device and the working channel is configured for aspiration and the method further comprising injecting rinsing liquid into the irrigation channel and aspiring the rinsing liquid from the working channel to rinse the major papilla.

9. The method of claim 7, wherein the images of the major papilla are generated using the device that has a camera as the image sensor.

10. The method of claim 7, wherein the images of the major papilla are generated using the device that has an ultrasonic probe as the image sensor.

11. A method of generating a common channel entry identification model using a computational device, the computational device comprising:

a processor;

a non-transitory computer-readable storage medium storing a set of instructions; and a communication module connected to a network, the method comprising executing the set of instructions to direct the processor to:

retrieve an image from an endoscopic image library of major papilla;

process the image to generate an encoded image;

process the encoded image to segment a feature to generate a segmented image;

identify a common channel entry point as one of the segmented features; and use the encoded images and the segmented images to train a machine learning model to generate a common channel entry identification model for the identification of a common channel entry point in a new image of major papilla, wherein the endoscopic image library of major papilla comprises images of treatment-naïve images of major papilla and images of major papilla after cannulation of the common channel generated by an ERCP scope.

12. The method of claim 11, wherein the images of the major papilla are taken under the same or similar conditions of the ERCP scope.

13. The method of claim 12, wherein the same or similar conditions of the ERCP scope including number of time the major papilla has been rinsed with a rinsing fluid, the amount of illumination light supplied to the image sensor, parameters used by the image sensor.

14. The method of claim 11, further comprising obtaining a plurality of images of major papilla using an ultrasound device interfaced the ERCP scope, the plurality of ultrasound images including treatment-naïve images of major papilla and images of major papilla after cannulation of the common channel, to add to the endoscopic image library of the major papilla.

15. A method of labeling an estimated duct entry point in a new image of major papilla of a patient during an ERCP using a computational device, the computational device comprising:

a processor;

a non-transitory computer-readable storage medium storing a set of instructions; and a communication module connected to a network, the method comprising executing the set of instructions to direct the processor to:

obtain an image of the major papilla of a patient from a live stream of images of the major papilla obtained through a camera of ERCP scope;

use the common channel entry identification model generated by claim 11 to analyze the image of the major papilla of the patient;

identify the common channel entry point in the image of the major papilla of the patient using the common channel entry identification model; and label the common channel entry point on the live stream images of the major papilla of the patient.

16. The method of claim 15, wherein the image of the major papilla of the patient is taken under the same or similar conditions of the image of claim 11.

17. A method of performing ERCP with the aid of Artificial Intelligence operated on a computational device, the device comprising:

a processor;

a non-transitory computer-readable storage medium storing a set of instructions; and a communication module connected to a network, the method comprising executing the set of instructions to direct the processor to:

label an estimated duct entry point in a new image of major papilla of a patient during an ERCP using the method of claim 15; and insert a guidewire from a working channel of the ERCP device to the estimated duct entry point to enter the common duct.

* * * * *